United States Patent [19]
Burger et al.

[11] Patent Number: 5,849,756
[45] Date of Patent: Dec. 15, 1998

[54] PHARMACEUTICAL COMPOSITION AND METHOD FOR MODULATING THE IMMUNE REACTION

[75] Inventors: Ulrich Burger, Geneva; Jean-Claude Jaton, Thonex; Fabrizio Marazza, Novaggio; Ari Lewenstein, Zurich, all of Switzerland; Francis M. Sirotnak, New York, N.Y.

[73] Assignee: Cerbios-Pharma SA, Barbengo, Switzerland

[21] Appl. No.: 450,491

[22] Filed: May 26, 1995

[30] Foreign Application Priority Data

May 27, 1994 [CH] Switzerland .............................. 1649/94

[51] Int. Cl.$^6$ ...................... C07D 209/34; C07D 215/50; A61K 31/405; A61K 31/47
[52] U.S. Cl. ......................... 514/311; 514/312; 514/415; 514/416; 514/418; 546/153; 546/154; 546/156; 546/157; 546/158; 548/452; 548/469; 548/472
[58] Field of Search ..................................... 514/311, 312, 514/412, 415, 416, 418; 546/153, 154, 156, 157, 158; 548/452, 469, 472

[56] References Cited

PUBLICATIONS

Beccalli, Egle M. et al. "Synthesis of Pyrrolo[1,2–c] quinazoline derivatives", Chemical Abstracts, Sep. 28, 1992, pp. 741–742, vol. 117, No. 13, Columbus, Ohio, US.

Horne, Stephen et al, "Rapid Synthesis of some indole alkaloids of the Calabar bean", Chemical Abstracts, Mar. 16, 1992, p. 807, vol. 116, No. 11, Columbus, Ohio, US.

Nonhebel, Heather M. et al, "Indole–3–acetic acid catabolism in Zea mays seedlings. Metabolic conversion of oxindole–3–acetic acid to 7–hydroxy–2–oxindole–3–acetic acid 7'–0–B–D–glucopyranoside",Chemical Abstracts, Dec. 9, 1985,p. 412, vol. 103, No. 23, Columbus, Ohio, US.

Tacconi, Gianfranco et al. "Heterodiene synthesis. Part XVII. Reactions of 2–oxoindolin–3–ylidene derivatives with enamines: a Michael path as an alternative to 1,2–and 1,4–cycloadditions", Chemical Abstracts, Mar. 28, 1977, p. 515, vol. 86, No. 13, Columbus, Ohio, US.

Mori, Miwako et al, "Reactions and synthesis with organometallic compounds, IV. New synthesis of oxindole derivatives by utilization of organonickel complex", Chemical Abstracts,Dec. 6, 1976, pp. 500–501, vol. 85, No. 23, Columbus, Ohio, US.

R.L. Autrey et al, "The synthesis and stereochemistry of some isatylideneacetic acid derivatives", Chemical Abstracts, Mar. 27, 1967, p. 5218, vol. 66, No. 13, Columbus, Ohio, US.

Hayashi, Hiroaki et al, "5–HT3 receptor antagonists 1. New Quinoline derivatives", Chemical Abstracts, Feb. 1, 1993, p. 668, vol. 118, No. 5, Columbus, Ohio, US.

Gordon N. Walker, "Synthesis of 5,6–dimethoxyindole–3–propionic acids and 6,7–dimethoxy–3,4–dihydrocarbostyrils, by reduction of nitro compounds", Chemical Abstracts, Jan. 25, 1960, col.1179–1180, vol. 51, No. 2, Columbus, Ohio, US.

Kumar, Balbir et al, "Photolytic cyclization of half–amides derived from maleic acid and m–anisidine and m–toluidine", Chemical Abstracts, Jan. 15, 1979, p. 556, vol. 90, No. 3, Columbus, Ohio, US.

Ide, Akio et al, "Synthesis of quinoline and isoquinoline derivatives. VIII. Photoreaction of 4–substituted quinoline N–oxide and 2(1H)–quinoline in propionic acid", Chemical Abstracts, Jan. 2, 1978, p. 567, vol. 88, No. 1, Columbus, Ohio, US.

*Primary Examiner*—Nathan M. Nutter
*Attorney, Agent, or Firm*—Shenier & O'Connor

[57] ABSTRACT

Pharmaceutical compositions for the modulation of the immune reaction of warm blooded animals that are derivatives of the 2-oxindole-3-acetic acid or the 2-oxo-1,2,3,4-tetrahydroquinoline-4-carboxylic acid are described, and whereby the derivatives can optionally be in an equilibrium with each other.

The derivatives included in the pharmaceutical compositions comprise those compounds which are already described in the literature and also new compounds.

Furthermore, new derivatives of the the 2-oxindole-3-acetic acid and the 2-oxo-1,2,3,4-tetrahydroquinoline-4-carboxylic acid are described, particularly also the the pure antipodes of the mixture of enantiomeres of the 2-oxo-1,2,3,4-tetrahydroquinoline-4-carboxylic acid.

22 Claims, No Drawings

PHARMACEUTICAL COMPOSITION AND METHOD FOR MODULATING THE IMMUNE REACTION

The present invention refers to pharmaceutical compositions for the modulation of the immune reaction of warm-blooded animals which are containing derivatives of the 2-oxindole-3-acetic acid or analogous derivatives of the 2-oxo-1,2,3,4-tetrahydroquinoline carboxylic acid as pharmaceutically active agent that can be in an equilibrium with each other and whereby one or more groups of a hexose can be bound to those derivatives. The pharmaceutically active agent included in the pharmaceutical compositions comprise new active agents as well as those that have already been described in the literature, but that have so far never been used as pharmaceutically active agent in any pharmacological composition.

Furthermore the invention refers to new derivatives of the 2-oxindole-3-acetic acid or the 2-oxo-1,2,3,4-tetrahydroquinoline-4-carboxylic acid, respectively.

DESCRIPTION OF THE PRIOR ART

Pharmaceutical compositions containing compounds as pharmaceutically active agent that are derivatives of the 1-oxindole-3-acetic acid, or the 2-oxo-1,2,3,4-tetrahydroquinoline-4-carboxylic acid, respectively, have so far not been described. Such compounds which are differing in their basic structure from said 2-oxo-1,2,3,4-tetrahydroquinoline-4-carboxylic acid by the fact that they have a double bond within the heterocyclic group and represent therefore derivatives of the 2-oxo-1,2-dihydroquinoline-4-carboxylic acid and which are furthermore present not as free acids, but in the form of esters with an alcohol component, in which the hydroxy group is linked to a basic azabicycloalkyl group, were examined by Hayashi, Hiroaki et al. with regard to their activity as 5-HT$_3$ receptor-antagonist. In this context, Chemical Abstract, Vol. 118, No. 5, Feb. 1, 1993, Columbus Ohio, USA, Abstract No. 38750 shall be mentioned which represents an abstract of the original text in J. Med. Chem. 1992, 35 (26), 4893–4902.

A few of the derivatives of the 2-oxindole-3-acetic acid, or the analogous derivatives of the 2-oxo-1,2,3,4-tetrahydroquinoline-4-carboxylic acid that are being used as pharmaceutically active agent in the pharmaceutical compositions according to the invention are however not new chemical compounds, but they have already been described in the literature.

The unsubstituted 2-oxindole-3-acetic acid and the unsubstituted 2-oxo-1,2,3,4-tetrahydroquinoline-4-carboxylic acid have already been described in the literature and these compounds have the following formulas Ia and IIa.

It is known since a long time (see the publication of A. J. Hill et al., Am. Chem. J., vol. 52, pages 769–775, 1930) that under hydrolytic conditions, the 2-oxindole-3-acetic acid of the formula Ia is in an equilibrium with the 2-oxo-1,2,3,4-tetrahydroquinoline-4-carboxylic acid of the formula IIa and this equilibrium reaction is being illustrated through an opening of the indole ring and a ring-extensive closure according to the following scheme:

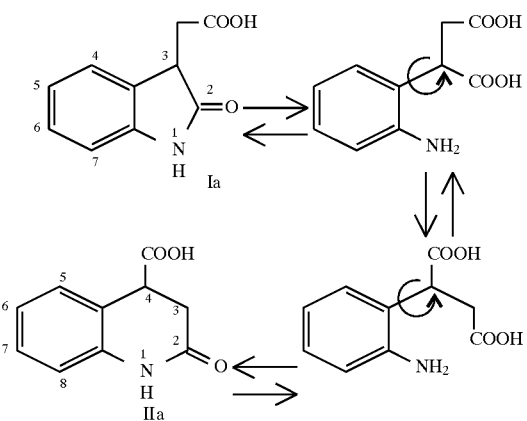

Under acid conditions the equilibrium is largely shifted to IIa.

The indole-3-acetic acid which is differing from the compound of the above mentioned formula Ia in the fact that in the position 2 of the indole ring, a CH$_2$-group is present, rather than the carbonyl group is described in the art. It is furthermore known to be a growth factor for plants which is eventually being transformed by corn (*Zea mays*)—seedlings via the 2-oxindole-3-acetic acid of the above mentioned formula to the corresponding derivative with a hydroxy substituent in the position 7 of the indole ring and thereafter to the corresponding glycoside (see the publication of H. M. Nonhebel et al. in The Journal of Biological Chemistry, Vol. 260(23), pages 12685–12689, 1985 and the corresponding abstract in Chemical Abstracts, Vol. 103, Dec. 9, 1985, Columbus, Ohio, USA; Abstract No. 193222a.)

The following derivatives of the 2-oxindole-3-acetic acid of the formula I, or the 2-oxo-1,2,3,4-tetrahydroquinoline-4-carboxylic acid of the formula II, respectively, have already been described in the litera- ture:

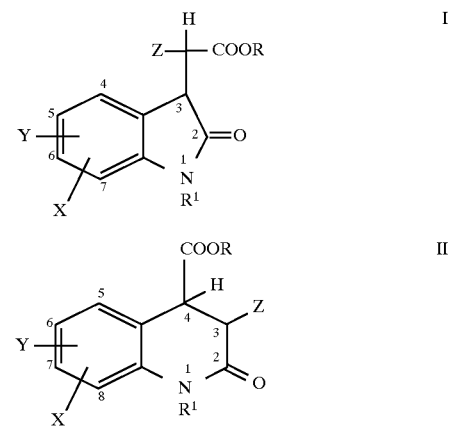

From the free carboxylic acids, in which R is a hydrogen atom, all those compounds are already known, in which Z is a hydrogen atom and R$^1$ is also a hydrogen atom, whereby the groups X and Y are both representing hydrogen, or the groups X and Y are chlorine or bromine atoms in the positions 6 and 8 of the benzene ring of the tetrahydroquinoline derivative of the formula II or one of the groups X and Y represents a bromine or iodine atom in the position 6 of the tetrahydroquinoline system and the other is a hydrogen atom, and furthermore those derivatives of the 2-oxindole-3-acetic acid of the formula I, in which R, $R^1$ and Z are representing hydrogen and one of the groups X and Y is equally hydrogen and the other of both groups is a hydroxyl group, bound to the benzene ring in the position 5 or the position 7 of the indole ring or represents an oxygen atom with a group of glucose bound to it, also in the position 7 of the indole ring.

Concerning the mentioned substituted derivatives of the 2-oxindole-3-acetic acid with hydroxyl groups or glucose esters bound to the benzene ring through an oxygen atom, the publication of P. Lewer, J. Chem. Soc. Perkin Trans. I, 1987, pages 753–757 has to be mentioned, as well, as the publications of H. M Nonhebel et al. in Plant Physiol., 1984, 76(4), pages 979–983 (see Chemical Abstracts, Vol. 102, No. 109920a). Concerning the chlorine-, bromine- and iodine substituted derivatives of the 2-oxo-1,2,3,4-tetrahydroquinoline-4-carboxylic acid the Beilstein, main publication, Vol. 22, page 308, or the supplementary edition II, Vol. 22, pages 242 and 243, have to be mentioned.

Furthermore the 2-oxo-1,2,3,4-tetrahydroquinoline-4-carboxylic acid of formula II has already been described, in which R, $R^1$, X and Y are representing hydrogen and Z is representing an ethyl group. In this context, the preparation of this quinoline derivatives through a photochemical ethylation, developed by Ide, Akio et al., has to be mentioned and reference is being made in this context concerning Chemical Abstracts, Vol. 88, No. 1, Jan. 2, 1978, Columbus Ohio, USA; Abstract No. 6684q, which is representing the abstract of the original work in Bull. Chem. Soc. Jpn 1977, 50(8), 1959–63.

Those 2-oxo-1,2,3,4-tetrahydroquinoline-4-carboxylic acid of the formula II, in which R, Z, $R^1$ and X are representing hydrogen and Y is signifying a methyl group or a methoxy group in the position 7 of the benzene ring of the compounds of the formula II, were synthesised by photolytical cyclisation from the corresponding carboxylic acids which have, instead of the nitrogen containing condensed heterocyclic group of the tetrahydroquinoline carboxylic acid, a correspondingly unsaturated aliphatic chain that is bound to the benzene ring via the $NR^1$ group. It was found that corresponding derivatives having a group Y which has the meaning of hydrogen, chlorine or nitro, can not be synthesised in an analogous manner through photocyclisation. Reference is being made in this context to the publication of Kumar, Baldev et al. which is summarised in Chemical Abstracts, Vol. 90, No. 3, Jan. 15, 1979, Columbus, Ohio, USA, Abstract No. 21934f and which is representing an abstract of the original publication in Indian J. Chem., Sect. B 1978, 16B(8), 729–30.

From the esters of the 2-oxindole-3-acetic acid of the formula I, or the 2-oxo-1,2,3,4-tetrahydroquinoline-4-carboxylic acid of the formula II those methyl esters are known, in which R is methyl and Z and $R^1$ are representing hydrogen and further X and Y are both standing for hydrogen or for two methoxy groups in the positions 5 and 6 of the benzene ring of the indole system or X and Y are both a group of the formula

equally in the positions 5 and 6 of the indole ring. The publication of S. J. McEnvoy et al in J. Org. Chem., Vol. 38, No. 19, 1973, pages 3350–3352, or Beilstein, system No. 3366, supplementary edition III/IV, Vol. 22, pages 3045 and 3046, main edition, Vol. 22, pages 307 and 308 is to be mentioned.

Furthermore the methyl ester of the 2-oxindole-3-acetic acid of the formula I has already been described in which R is methyl, Z, X and Y represent hydrogen and the group $R^1$ is a methyl substituent. This methyl ester of the 1-methyl-2-oxindole-3-acetic acid of the formula I was synthesised through cyclisation by use of an organo-nickel complex and in this respect the publication of Mori, Miwako et al. "Reactions and Syntheses ... ", Chemical Abstracts, Vol. 85, No. 23, Dec. 6, 1976, Columbus, Ohio, USA, Abstract No. 177179w has to be mentioned which is representing an abstract of the corresponding original work in Tetrahedron Lett. 1976 (21), 1807–1810.

Also the methyl ester of the unsubstituted 2-oxo-1,2,3,4-tetrahydroquinoline-4-carboxylic acid, which is the compound of the formula II, has already been described in the literature, in which R is methyl and Z, $R^1$, X and Y are representing hydrogen. Reference is being made in this context to the publication of J. A. Aeschlimann in Soc. 1926, pages 2902–2908.

Ethyl esters of the 2-oxindole-3-acetic acid of the formula I, or the 2-oxo-1,2,3,4-tetrahydroquinoline-4-carboxylic acid of the formula II, respectively, have already been described in the literature.

Thus the ethyl ester of the unsubstituted 2-oxindol-3-acetic acid is known, that is the compound of the formula I, in which R is ethyl and $R^1$, X and Y are representing hydrogen (see Beilstein, supplementary edition III/IV, Vol. 22, page 3047), Also ethyl esters of the 2-oxindole-3-acetic acid in which the group $R^1$ is representing a methyl group or an acetyl group have already been described in the literature. For example the corresponding compounds of the formula I, in which R is standing for ethyl, $R^1$ represents methyl, Z and X are signifying hydrogen and Y is representing either also hydrogen or methoxy in the position 5 of the benzene ring of the indole acetic acid, are used as starting material for the preparation of some indole alkaloides of the calabar beans. In this context the publication of Horne, Stephen et al., Chemical Abstracts, Vol., 116, No. 11, Mar. 16, 1992, Columbus, Ohio, USA; Abstract No. 106567u has to be mentioned, in which the original work of J. Chem. Soc., Perkin Trans. 1, 1991, (12) 2047–51 is being summarised.

Also the ethyl ester of the unsubstituted 2-oxo-1,2,3,4-tetrahydroquinoline-4-carboxylic acid, which is the compound of the formula II, in which R is ethyl and Z, $R^1$, X and Y are representing hydrogen, are already known (see Beilstein, supplementary edition III/IV, Vol. 22, pages 3045 and 3046).

The 2-oxindole-3-acetic acid of the formula I, or the 2-oxo-1,2,3,4-tetrahydroquinoline-4-carboxylic acid of the formula II, respectively, in which R, Z, X and Y are representing hydrogen atoms and $R^1$ signifies a methyl group, a phenyl group, a benzyl group, an acetyl group or the acyl group of the p-chloro-benzoic acid, that is the 4-chlorobenzoyl group, have already been described as well (see Beilstein, system No. 3366, supplementary edition II, Vol. 22, page 242, or main edition, respectively, Vol. 22, page 308).

From the 2-oxindole-acetic acids of the formula I, in which $R^1$ is a benzyl group, furthermore the methyl- and the ethyl ester is already known.

Furthermore those 2-oxo-1,2,3,4-tetrahydroquinoline-4-carbocylic acids of the formula II are already known, in which Z, X and Y are hydrogen and $R^1$ is phenyl, both the free acid as well as the methyl ester.

Also those 2-oxo-1,2,3,4-tetrahydroquinoline-4-carbocylic acids of the formula II are known, in which Z, X and Y are hydrogen and $R^1$ is butyl, both the corresponding free acid as well as the butyl ester and the ester of a specific bicyclic alkanol.

None of the known derivatives of the formula I, or II respectively has been used in any pharmaceutical as active agent.

A variety of carboxylic acid amides of the 2-oxo-1,2,3, 4-tetrahydroquinoline-4-carboxylic acid, in which instead of the group of the formula —COOR (see formula II) a carboxylic acid amide group of the formula—$CON(R_3)_2$ is present, whereby the group $N(R_3)_2$ is stemming from a substituted piperazinyle, however have been examined with regard to their effect as positive inotropic agents or their effect concerning the influence of the heart rhythm, respectively, whereby the carboxylic acid amide group of the given structure is either in the position 4 or on other positions of the heterocyclic ring or on the benzene ring of the 2-oxo-1,2,3,4-tetrahydroquinoline-4-carboxylic acid derivative. It was thereby found that only those compounds have showed a corresponding effect, in which the carboxylic acid amide group is bound to the position 6, that is bound to the benzene ring, while the corresponding carboxylic acid amide group in the position 4 (see formula II) of the tetrahydroquinoline structure was ineffective. In this context the publication of M. Tominaga et al. in Chem. Pharm. Bull., Vol. 34 (1986), pages 682–689, particularly the tables V on page 689 have to be mentioned.

DESCRIPTION OF THE INVENTION

A subject of the present invention is a pharmaceutical composition for the modulation of the immune reaction of warm blooded animals, that is characterised in that it contains as pharmaceutically active agent a derivative of the 2-oxindole-3-acetic acid of the formula I, or a corresponding derivative of the 2-oxo-1,2,3,4-tetrahydroquinoline-4-carboxylic acid of the formula II,

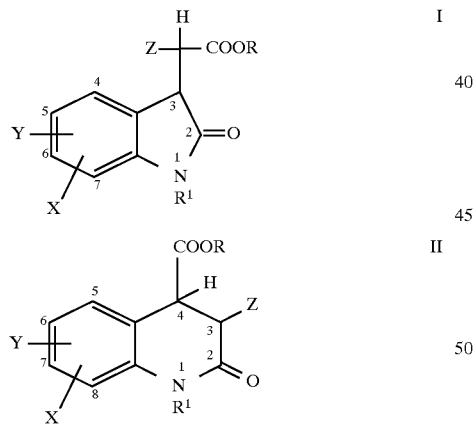

whereby the compound of the formula I is optionally in an equilibrium with the compound of the formula II, and
$R^1$ is representing a hydrogen atom, an alkyl group with 1–6 carbon atoms, an aralkyl group with 1–6 carbon atoms in the alkyl part, a cycloalkyl group or an acyl group of the formula

in which $R^4$ is a hydrogen atom, an alkyl group with 1–6 carbon atoms, an aralkyl group with 1–6 carbon atoms in the alkyl part, an aryl group or a cycloalkyl group, Z is a hydrogen atom, an alkyl group with 1–6 carbon atoms, an aralkyl group with 1–6 carbon atoms in the alkyl part, cycloalkyl group, or a an aryl group, and X and Y are representing independent from each other hydrogen atoms, alkyl groups, cycloalkyl groups, aryl groups, hydroxy groups, halogen atoms, nitro groups, ether groups of the formula

ester groups of the formula

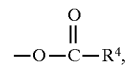

or ester groups of the formula

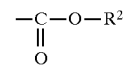

whereby in the above mentioned formula the group
$R^4$ has the above identified meaning and the group
$R^2$ represents an alkyl group with 1–6 carbon atoms, an aralkyl group with 1–6 carbon atoms in the alkyl part, a cycloalkyl group, or an aryl group or the groups X and Y are together representing a group of the formula

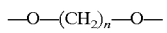

in which
n is an integer in the range of 1–4 and
R is a hydrogen atom, an alkyl group with 1–6 carbon atoms, an aralkyl group with 1–6 carbon atoms in the alkyl part, a cycloalkyl group or an aryl group or the group R is representing a hexose group bound as an ester or a chain of 2–6 hexose groups, whereby the hexose group or one or more hexose groups further carry, optionally, substituents, for example, hydroxy groups of those sugar groups that are acylated and
whereby the pharmaceutically active agent of the formulas I or II, respectively, as well as all above defined derivatives, are present in a free form or in the form of pharmaceutically acceptable salts, or whereby the pharmaceutically active agent is representing a mixture containing at least two of the above defined derivatives or their pharmaceutically acceptable salts.

As can be seen from the chemical structure of the derivatives of 2-oxindole-3-acetic acid of the formula I, those compounds have a chiral center in the position 3 of the indole ring, in which Z is a hydrogen atom and those compounds in which Z is one of the mentioned hydrocarbon groups, have one more chiral center, namely the carbon atom, to which this group Z is bound.

Furthermore also the 2-oxo-1,2,3,4-tetrahydroquinoline-4-carboxylic acids of the formula II, in which Z is a hydrogen atom, have a chiral center in the position 4 of the tetrahydroquinoline system and those compounds of the formula II, in which Z is one of the mentioned hydrocarbon groups, have one more chiral center, namely the carbon atom in the position 3 of the tetrahydroquinoline system.

In the literature, exclusively racemates of the 2-oxindole-3-acetic acid and the derivatives thereof of the formula I and also of the 2-oxo-1,2,3,4-tetrahydroquinoline-4-carboxylic acid of the formula II and the derivatives thereof, have been described.

For the first time the separation of the unsubstituted 2-oxo-1,2,3,4-tetrahydroquinoline-4-carboxylic acid of the formula II has now been carried out, that is the derivative, in which all groups Z, R, $R^1$, X and Y are hydrogen.

From the racemate of the unsubstituted 2-oxo-1,2,3,4-tetrahydroquinoline-4-carboxylic acid of the formula II both enantiomeres have been isolated in pure form. Those optically active antipodes are representing new chemical compounds.

A further subject of the present invention are those new compounds of the formula II which are characterised in that they have the following formula IIb

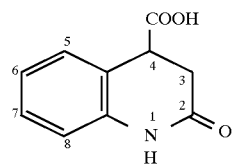

IIb and they are present in the form of the optically active enantiomeres.

In the inventive pharmaceutical compositions, a racemate of the compound of the formula I and II, respectively, or a form enriched with one of the optical antipodes or the pure form of the optical antipodes of the compound of the formula I or II can be contained.

Preferred pharmaceutically active agents which are included in the pharmaceutical compositions according to the invention, are those compounds of the formula I or II, respectively, in which Z and $R^1$ represent a hydrogen atom, R is representing a hydrogen atom, an alkyl group with 1–6 carbon atoms, a cycloalkyl group with 3–8 carbon atoms or an aryl group, preferably a phenyl group or a substituted pheny group and X and Y are independently from each other hydrogen atoms, hydroxy groups, halogen atoms, nitro groups or ether groups of the formula

or ester groups of the formula

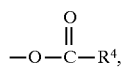

whereby in those groups the group $R^2$ represents an alkyl group with 1–6 carbon atoms or an aryl group, preferably an unsubstituted or substituted phenyl group and $R^4$ is an alkyl group with 1–6 carbon atoms, an aryl group, preferably an unsubstituted or substituted phenyl group or a cycloalkyl group with 3–7 carbon atoms.

Particularly preferred pharmaceutically active agents are those compounds of the formula I or II, respectively, in which all groups R, Z, X, Y and $R^1$ are representing hydrogen.

The pharmaceutically active agents of the formula I and II included in the pharmaceutical compositions according to the invention are comprising new compounds as well as those compounds that have already been described in the literature that have however now yet been employed in any pharmaceutical composition as pharmaceutically active agent.

The pharmaceutically active agents of the formula I or II, respectively, were synthesised according to procedures that have already been described in the literature. Thus it is possible for example to synthesise the 2-oxindole-3-acetic acid through oxidation of indole-3-acetic acid, according to the procedure that has been described by Szabo-Pisztay, L. Szabo, in Synthesis 1979, 176.

The derivatives of the 2-oxindole-3-acetic acid can for example be prepared from the unsubstituted compound through corresponding substitution reactions, e.g. halogenations, nitrations, ester formation and similar known procedures.

It is also possible, through use of correspondingly substituted starting materials, to prepare the product with the desired substitution according to known preparation procedures.

Furthermore it is possible to transform the unsubstituted 2-oxindole-3-acetic acid through treatment with two-normal hydrochloric acid to the unsubstituted 2-oxo-1,2,3,4-tetrahydroquinoline-4-carboxylic acid (see the equilibrium between the compound of the formula Ia and the formula IIa).

Furthermore it is possible, e.g. according to the procedure described by R. C. Elderfield, H. H. Rembges, in J. Org. Chem. 32/1967, page 3809, to introduce the acetic acid side-chain of the formula

in a corresponding indole derivative. In this context the procedures of preparation described by P. L. Julian et al., in J. Am. Chem. Soc., Vol. 75, 1953, pages 5305–5309 and by J. A. Aeschlimann, in J. Chem. Soc., 1926, pages 2902–2912 has to be mentioned.

From the unsubstituted 2-oxo-1,2,3,4-tetrahydroquinoline-4-carboxylic acid of the formula II, new derivatives of this acid can be prepared through corresponding substitution reactions and further reaction steps.

The known as well as the new pharmaceutically active agents of the formulas I, or II, respectively, in which the substituents R, $R^1$, Z, X and Y have the above mentioned significance, had the surprisingly high effectiveness concerning the modulation of the immune reaction.

A further subject of the present invention are new chemical compounds of the formulas I and II.

A category of these new chemical substances are those of the formulas I and II

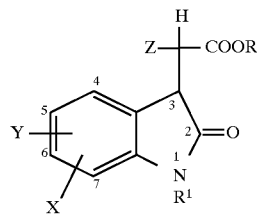

I

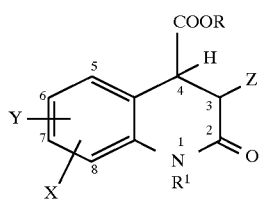

II in which $R^1$ is representing a hydrogen atom, an alkyl group with 1–6 carbon atoms, an aralkyl group with 1–6 carbon atoms in the alkyl part, a cycloalkyl group or an acyl group of the formula,

in which $R^4$ is a hydrogen atom, an alkyl group with 1–6 carbon atoms, an aralkyl group with 1–6 carbon atoms in the alkyl part, an aryl group or a cycloalkyl group, Z is a hydrogen atom, an alkyl group with 1–6 carbon atoms, an aralkyl group with 1–6 carbon atoms in the alkyl part, a cycloalkyl group or an aryl group, and X and Y are independently hydrogen atoms, alkyl groups, cycloalkyl groups, aryl groups hydroxy groups, halogen atoms, nitro groups, ether groups of the formula

ester groups of the formula

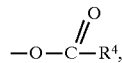

ester groups of the formula

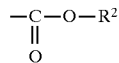

and whereby in the above mentioned formulas the group
$R^4$ has the above mentioned significance and the group
$R^2$ is representing an alkyl group with 1–6 carbon atoms, an aralkyl group with 1–6 carbon atoms in the alkyl part, a cycloalkyl group or an aryl group or the groups X and Y are representing both a group of the formula

in which
n is an integer in the range of 1–4 and
R is representing a hydrogen atom, an alkyl group with 1–6 carbon atoms, an aralkyl group with 1–6 carbon atoms in the alkyl part, a cycloalkyl group or an aryl group or an ester-like bound hexose group or a chain of 2–6 hexose groups, whereby the hexose group or one or more of the hexose groups furthermore carry, optionally, substituents, e.g. hydroxy groups of these sugar groups that are acylated,
provided that in those compounds of the formula I or II, respectively, in which
R is a hydrogen atom or a methyl group or an ethyl group, and further
$R^1$ is signifying a hydrogen or methyl and furthermore Z is hydrogen,
the groups X and Y must not have both the meaning of two hydrogen atoms, two chlorine atoms, two bromine atoms, two methoxy groups or the group of the formula —O—$CH_2$—O, and furthermore in the case that the group X is hydrogen, the group Y must have a different meaning than a iodine atom, a hydroxy group, a methoxy group or a methyl group and
furthermore provided that in those compounds of the formula I or II, in which Z. X and Y are signifying a hydrogen atom and R is hydrogen, methyl, ethyl or butyl, the group $R^1$ must have a different meaning than the one of a methyl group or a butyl group, a benzyl group, an acetyl group or a 4-chlorobenzoyl group and furthermore
provided that in those 2-oxo-1,2,3,4-tetrahydroquinoline-4-carboxylic acids of the formula II, in which Z is an ethyl group, at least one of the groups R, $R^1$, X and Y must have a different meaning than the one of a hydrogen atom
as well as salts of these new pharmaceutically active agents of the formula I or II, respectively.

Preferred new chemical compounds of the formula I or II, respectively, are the corresponding esters of the designated formulas, in which
R is an alkyl group with 3–6 carbon atoms, an aralkyl group with 1–6 carbon atoms in the alkyl part, in which the aryl group is a phenyl group or a substituted phenyl group, a cycloalkyl group with 3–7 carbon atoms, an aryl group, preferably a substituted or unsubstituted phenyl group, or is representing an ester-like bound hexose group or a group of 2–6 hexose groups, e.g. glucose groups, whereby, optionally, those hexose groups are substituted, and whereby
the groups $R^1$, Z, X and Y have the above mentioned significance, whereby however,
if $R^1$ is a butyl group and Z. X and Y are representing hydrogen, the group R must have a different meaning than a butyl group,
and whereby those compounds of the formula I or II are present in free form or in the form of salts.

In the case that in those esters of the formula I or II, respectively, the group R represents an ester-like bound hexose group or a group of 2–6 hexose groups, those sugar groups can, optionally, carry further substituents which are bound to them, namely, preferably through hydroxy groups of the corresponding hexose groups. It is also possible that to such a hexose group bound on an ester group, an aglycone group could be linked, or that a chain of 2–6 hexose groups is interrupted through an aglycone group. Examples are aglycones which are bound through ether bonds or ester bonds to the hydroxy groups of the hexose groups.

A preferred group of substituents are such which are bound to the fundamental structure through an ether bond, which means corresponding hexose groups, in which instead of one or more of the hydroxy groups, corresponding groups of the formula —$OR^6$ are present, in which $R^6$ is representing an ether-like bound group is representing a bivalent organic group that is linking two different hydroxy groups of an hexose group or two different hexose groups, for example under formation of the structure of a cyclic diether.

A further preferred category of substituents which can be bound to the corresponding hexose groups, are those hexose groups, in which one or more hydroxy groups—are acylated, particularly through acyl groups which are derived from aromatic, alicyclic or aliphatic carboxylic acids, e.g. formic acid, acetic acid or propionic acid. Also in this case, optionally, two different hydroxy groups bound to hexose groups, can be linked through an acyl group of a bivalent acid and for example two hydroxy groups can be transformed through acylation with an active derivative of the carbonic acid to a structure of the formula

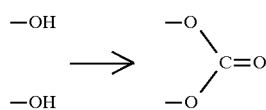

or though acylation with a dicarboxylic acid to a structure of the formula

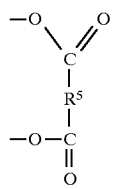

In the case that the dicarboxylic acid is maleic acid, $R^5$ is representing —$CH_2$—.

A further preferred group of new chemical compounds of the formula I or II, respectively, are the corresponding free carboxylic acids, which means those compounds of the formula I or II, respectively, in which R is hydrogen and further Z is representing an alkyl group with 1–6 carbon atoms, an aralkyl group with 1–6 carbon atoms in the alkyl part, in which the aryl group is preferably an unsubstituted or substituted phenyl group, a cycloalkyl group with 3–7 carbon atoms or an aryl group, preferably a substituted or unsubstituted phenyl group and X, Y and $R^1$ have the above mentioned significance, provided that, if in those acids Z is an ethyl group, at least one of the substituents $R^1$, X and Y must have a different meaning, than the one of a hydrogen atom and whereby those compounds of the formula I or II, respectively, are present in a free form or in the form of salts.

A further preferred category of compounds according to the invention of the formula I or II, respectively, are those, in which the groups R, Z and $R^1$ have the above mentioned meaning and at least one of the groups X and Y have the meaning of alkyl groups with at least 2 carbon atoms, cycloalkyl groups, phenyl groups, nitro groups, alkoxy groups with at least 2 carbon atoms or ester groups of the formula

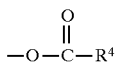

whereby in this group $R^4$ is an alkyl group with 1–6 carbon atoms, an aryl group, preferably an unsubstituted or substituted phenyl group or a cycloalkyl group with 3–7 carbon atoms, whereby however, if at least one of the groups R, Z or $R^1$ has a different meaning than a hydrogen atom, the group X and/or the group Y can furthermore have the meaning of methyl groups and/or methoxy groups, whereby however, if in those compounds of the formula I, Z and $R^1$ are hydrogen and R is methyl and both groups X and Y are standing for methoxy groups, they must not be situated in the position 5 and 6 of the benzene ring of the indole system of the compound of the formula I.

Concerning the pharmaceutical activity of the active agent included in the pharmaceutical compositions it was found that they are causing a modulation of the immune reaction of warm blooded animals, by stimulating the formation of lymphokinines and through this stimulation for example the formation of interferon can be stimulated and/or the formation of TNF-factors (tumor-nectrosis factors) can be stimulated.

Furthermore it was found that the pharmaceutically active agents in the pharmaceutical compositions according to the invention are being inhibited, if those additional factors are present that are leading to an inhibition of the stimulation of the macrophages or to an inhibition of the stimulation of the T-cells.

The modulation of the immune reaction through the pharmaceutical compositions according the invention have been tested on mice according to the PCT-test. It was found that a significant effectiveness could be achieved, if the corresponding compositions have been administered to the animals in a dosage per day of only 0.02 to 0.06 mg/kg body weight of the animal.

Through administration of the pharmaceutical compositions according to the invention the life expectancy of mice, in which different cancer cells have been implanted (e.g. prostate cancer, breast cancer etc.), could be considerably increased, in comparison to the group without administration of the corresponding compositions.

The pharmaceutical compositions according to the invention containing the known or new pharmaceutically active agents of the formula I or II, could for example be used for treatment of tumors, a variety of virus diseases, e.g. Aids and other abnormal syndroms which are caused through a reduced immune reaction.

Some embodiments of the invention are being illustrated through the following examples:

EXAMPLE 1

Preparation of 2-oxindole-3-acetic acid

The compound, designated in the title, corresponds to the formula I, whereby all substituents R, $R^1$, Z, Y and X are hydrogen. The preparation of this compound took place according to the method described by K. Szabo-Pisztay, L. Szabo in Synthesis 1979, 276.

To a solution of 20 g (1.14 mmol) of indole-3-acetic acid in 8.1 ml (1.14 mmol) of dimethylsulfoxide 19.3 ml (228 mmol) of concentrated hydrochloric acid is being added slowly. The reaction was strongly exothermic, whereby the dimethylsulfoxide was reduced to dimethylsulfide. The reaction mixture became dark violet and a huge quantity of precipitate was forming. The reaction mixture was left for four hours at room temperature and was thereafter diluted with 20 ml of water, the pH was adjusted to a value between 5 and 6 through the addition of concentrated aqueous ammonia solution and was extracted three times with 200 ml of ethyl acetate. The separated organic phases were gathered and washed once with 200 ml of water, dried over dry magnesium sulphate and evaporated under reduced pressure. The residue was dissolved in warm water, filtered and the water evaporated under reduced pressure.

Through crystallisation from a mixture of acetone+hexane, 7.5 g of yellowish crystals, corresponding to a yield of 34% of the theoretical value, were obtained.

The product had a melting point of 140° to 142° C. which was in agreement with the value of the literature.

In the nuclear resonance spectre the following signals were obtained:

$^1$ H—NMR (90 MHz, Py—D$_5$): 3.43 (dxd, J$_1$=9, J$_2$=15, 1 H, H—C(1')), 3.83 (dxd, J$_2$15, J$_3$=4.5, 1 H, H—C(1')), 4.46 (dxd, J$_1$=9, J$_3$=4.5, 1 H, H—C(3)), 7.2–7.6 (m, 3 H, arom.), 7.86 (d, J=7.5, 1 H, arom.).

EXAMPLE 2

Preparation of 2-oxo-1,2,3,4-tetrahydroquinoline-4-carboxylic acid

The compound mentioned in the title corresponds to the formula, whereby all group R, R$^1$, Z, X and Y had the meaning of hydrogen atoms.

The preparation was performed according to the method described by R. C. Elderfield, H. H. Rembges in J. Org. Chem. 32 (1967), 3809, as well as through rearrangement of the 2-oxindole-3-acetic acid prepared according to the example 1 under formation of the acid mentioned in the title.

To this purpose a suspension of 3 g (15.7 mmol) of the 2-oxindole-3-acetic acid obtained according to example 1 was heated to 100° C. in 150 ml of a 2 normal hydrochloric acid and this temperature was maintained during 2½ hours. After evaportion of the solvent, the solid residue was recrystallised from methanol and dried under reduced pressure.

Thus 1.63 g of uncoloured crystals were obtained which turned out to be the pure product through thin layer chromatography (silica gel, MeOH/EtOAc 1.3+1 drop of AcOH).

This product had a melting point of 219°–221° C. and this melting point was identical to the once of products that have been prepared according to methods described in the literature and also the melting point of the mixture of both products was identical.

The nuclear resonance spectrum was delivering the following signals:

$^1$ H—NMR (90 MHz, Py—D$_5$): 3.26 (dxd, J$_1$=7.5, J$_2$=16.5, 1 H, H—C (3)), 3.72 (dxd, J$_2$=16.5, J$_3$=4, 1 H, H—C(3)), 4.53 (dxd, J$_1$=7.5, J$_3$=4, 1 H, H—C(4)), 7.2–7.5 (m, 3 H, arom.), 7.93 (d, J=7.5, 1 H, arom.), 11.6 (s br., 1 H, H—N).

EXAMPLE 3

Performance of Pharmacological Tests with the Compounds Prepared According to Example 1 and Example 2

For the determination of the biological activity the PCV-test was carried out. The term PCV is based on the English expression Packed Cell Volume.

Swiss mice were purchased at the NCl (Cr:SW) and used for the test, as soon as the females were 5–7 weeks old and had a weight of 19–22 g.

At the day 0, to each animal 1.5×10$^5$ tumor cells S180 were administered through intraperitonal injection.

At the day 1 the animals were classified in separate groups, according to the random principle, whereby each groups was comprising 6 mice and in each group the animals were showing a similar weight. The weight of all animals of the group was noted.

In this test the unsubstituted 2-oxo-1,2,3,4-tetrahydroquinoline-4- carbocyclic acid of the formula II prepared according to example 2, as well as the unsubstituted 2-oxindole-3-acetic acid prepared according to example 1 were tested.

The acid of the formula II or the formula I, respectively were dissolved in a phosphate buffer solution of a pH of 7 (abbreviated as PBS). In some cases it was necessary to add a small quantity of sodium bicarbonate, in order to achieve a complete dissolution through increase of the pH from 7 to 7.5. The administration of the PBS-solutions was taking place through intraperitonal injections, administered daily, starting with the first day to the 5th day, such that per animal a total of 5 injections was administered.

Each animal received 0.2 ml of PBS-solutions of different concentration in order to achieve the daily dosage per mice according to the following table. To the mice of the group of comparison, only 0.2 ml of PBS without any pharmaceutically active agent were administered. The PBS-solutions of the compound of the formula II or the compound of the formula I, respectively, were prepared every day and diluted to the corresponding concentration.

At the 7th day or the 8th day, the mice of the control group were showing visibly swollen abdomen. The interpretation of the tests was accordingly taking place at the 7th or 8th day.

Execution of the Interpretation

Step (a): The weight of all mice of each group was separately taken and the mice were killed. A micro capillary tube was filled with the liquid existing in the abdominal cavity (ascites-liquid), by cutting the abdominal wall of each mouse.

Each sample was submitted to centrifugation during 7 minutes at 10,000 rpm (international cytocrit-centrifuge). The percentage of the cell volume (Vc) of each sample was measured.

Step (b): The liquid of the abdominal cavity of each animal was removed through drainage and the opened abdominal cavity dried using an absorbing tissue. The weight of the mice was again taken and the difference of the body weight was representing the volume of the liquid in the abdominal cavity (volume Va) of each mouse. In this case it was assumed that the body liquid had a specific mass of 1.0

Step (c): Calculation of the PCV

The PCV was calculated according to the following formula: PCV=%Vc×Va ml.

The average PCV for each group of animals (group T) treated with different quantities of the compound according to the formula II or I, respectively, and the PCV of the animals of the group for comparison purposes was calculated and therefrom was further calculated the value T/C for each of the treated groups.

A value T/C of 0.5 shows accordingly that a 50% growth of the cells took place, compared with the growth of the cells in the non-treated group for comparison purposes.

The results of these tests are summarised in the following table.

The given values are the average value of two tests which have been carried out with 6 or 7 mice per group. In the first column the number of the group is designated, whereby the group 1 is corresponding to the group for comparison purposes, where the animals were each treated with 0.2 ml of PBS, without any pharmaceutically active agent.

In the groups 2–7, PBS was administered which contained the designated quantities of the unsubstituted 2-oxindole-3-acetic acid of the formula I and in the groups 8–13 0.2 ml of PBS was injected, containing the designated quantities of unsubstituted 2-oxo-1,2,3,4-tetrahydroquinoline-4-carbocylic acid of the formula II. In the latter case the pH was adjusted to 7.5 by adding sodium bicarbonate, in order to achieve a complete dissolution of the acid of the formula II.

In the group for comparison purposes two series of tests each comprising 7 animals were performed and accordingly totally 14 animals was tested. In the groups 2–13, for each test, 6 animals were tested and two series of tests performed, that is for each group totally 12 animals was tested.

All animals were killed at the seventh day and submitted to the above described experiments. For this reason also in the group for comparison purposes the tumor S180 had developed in no animal that far that a natural death took place. Thus, all animals in each group, have survived until the seventh day.

In the third column of the following table, for each group of the tested animals the average gain of weight of the animals is indicated in g for each of the test groups 1–13 from the beginning of the test (day 0) to day 7 (day of killing).

| group No | dosage in mg/mouse | Gain in weight in g | PCV (µl) | T/C |
|---|---|---|---|---|
| 1 | 0 | +2.4 | 470 | 1.0 |
| 2 | 0.02 | +2.0 | 0 | 0.0 |
| 3 | 0.01 | +2.0 | 0 | 0.0 |
| 4 | 0.005 | +2.2 | 0 | 0.0 |
| 5 | 0.0025 | +1.7 | 0 | 0.0 |
| 6 | 0.00125 | +1.4 | 75 | 0.16 |
| 7 | 0.000625 | +2.5 | 169 | 0.36 |
| 8 | 0.02 | +2.2 | 0 | 0.0 |
| 9 | 0.01 | +2.0 | 0 | 0.0 |
| 10 | 0.005 | +1.5 | 0 | 0.0 |
| 11 | 0.0025 | +1.6 | 0 | 0.0 |
| 12 | 0.00125 | +1.0 | 139 | 0.29 |
| 13 | 0.000625 | +1.5 | 291 | 0.62 |

We claim:

1. A pharmaceutical composition comprising as the pharmaceutically active agents 2-oxindole-3-acetic acid of formula I and 2-oxo-1,2,3,4-tetrahydroquinoline-4-carboxylic acid of formula II

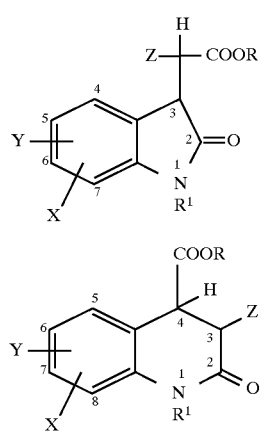

the compounds of formulas I and II being in equilibrium with one another in an aqueous solution of predetermined pH, wherein $R^1$ is a hydrogen atom, an alkyl group with 1–6 carbon atoms, an aralkyl group with 1–6 carbon atoms in the alkyl portion, a cycloalkyl group, or an acyl group of the formula

wherein $R^4$ is a hydrogen atom, an alkyl group with 1–6 carbon atoms, an aralkyl group with 1–6 carbon atoms in the alkyl portion, an aryl group, or a cycloalkyl group, Z is a hydrogen atom, an alkyl group with 1–6 carbon atoms, an aralkyl group with 1–6 carbon atoms in the alkyl portion, a cycloalkyl group, or an aryl group, and X and Y represent independently from each other hydrogen atoms, alkyl groups, cycloalkyl groups, aryl groups, hydroxy groups, halogen atoms, nitro groups, ether groups of the formula

ester groups of the formula

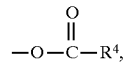

or ester groups of the formula

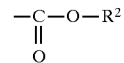

wherein $R^4$ is a hydrogen atom, an alkyl group with 1–6 carbon atoms, an aralkyl group with 1–6 carbon atoms in the alkyl portion, an aryl group, or a cycloalkyl group; $R^2$ is an alkyl group with 1–6 carbon atoms, an aralkyl group with 1–6 carbon atoms in the alkyl portion, a cycloalkyl group, or an aryl group or groups, or X and Y together represent a group of the formula

in which n is an integer between 1–4, and

R is a hydrogen atom, an alkyl group with 1–6 carbon atoms, an aralkyl group with 1–6 carbon atoms in the alkyl portion, a cycloalkyl group, an aryl group, a hexose group linked as an ester, or a chain of 2–6 hexose groups.

2. A pharmaceutical composition as in claim 1 wherein the aqueous solution is buffered.

3. A pharmaceutical composition as in claim 1 wherein the aqueous solution includes a phosphate buffer.

4. A pharmaceutical composition as in claim 1 wherein the aqueous solution has a pH of about seven.

5. A pharmaceutical composition as in claim 1 wherein the aqueous solution has a pH greater than seven.

6. A pharmaceutical composition as in claim 1, wherein

Z and $R^1$ are hydrogen atoms,

R is a hydrogen atom, an alkyl group with 1–6 carbon atoms, a cycloalkyl group with 3–8 carbon atoms or a phenyl group and X and Y are independently selected from hydrogen atoms, hydroxy groups, halogen atoms, nitro groups, ether groups of the formula

or ester groups of the formula

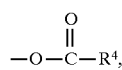

wherein R² is an alkyl group with 1–6 carbon atoms or a phenyl group; R⁴ is an alkyl group with 1–6 carbon atoms, a phenyl group, or a cycloalkyl group with 3–7 carbon atoms.

7. A pharmaceutical composition as in claim 1, wherein the pharmaceutically active agent comprises a racemate of the compound of formula I, a racemate of the compound of formula II, one or both of said racemates enriched with an enantiomer of formula I or II, or an enantiomer of formula I or II.

8. A pharmaceutical composition as in claim 6, wherein R, Z, X, Y and R¹ are all hydrogen atoms.

9. A pharmaceutical composition as in claim 6, wherein the pharmaceutically active agent comprises a racemate of the compound of formula I, a racemate of the compound of formula II, one or both of said racemates enriched with an enantiomer of formula I or II, or an enantiomer of formula I or II.

10. A pharmaceutical composition as in claim 7, wherein R, Z, X, Y and R¹ are all hydrogen atoms.

11. A pharmaceutical composition of the formula IIb

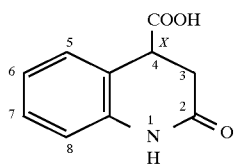

wherein the composition is present in the form of the optically active enantiomers.

12. A pharmaceutical composition of formula I or II,

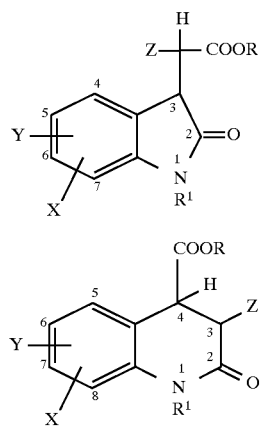

wherein

R¹ is a hydrogen atom, an alkyl group with 1–6 carbon atoms, an aralkyl group with 1–6 carbon atoms in the alkyl portion, a cycloalkyl group, or an acyl group of the formula

wherein R⁴ is a hydrogen atom, an alkyl group with 1–6 carbon atoms, an aralkyl group with 1–6 carbon atoms in the alkyl portion, an aryl group or a cycloalkyl group, Z is a hydrogen atom, an alkyl group with 1–6 carbon atoms, an aralkyl group with 1–6 carbon atoms in the alkyl portion, a cycloalkyl group or an aryl group, and X and Y represent independently from each other hydrogen atoms, alkyl groups, cycloalkyl groups, aryl groups, hydroxy groups, halogen atoms, nitro groups, ether groups of the formula

ester groups of the formula

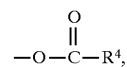

or ester groups of the formula

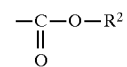

wherein R⁴ is a hydrogen atom, an alkyl group with 1–6 carbon atoms, an aralkyl group with 1–6 carbon atoms in the alkyl portion, an aryl group or a cycloalkyl group; R² is an alkyl group with 1–6 carbon atoms, an aralkyl group with 1–6 carbon atoms in the alkyl portion, a cycloalkyl group or an aryl group or groups, or X and Y together represent a group of the formula

in which n is an integer between 1–4, and

R is a hydrogen atom, an alkyl group with 1–6 carbon atoms, an aralkyl group with 1–6 carbon atoms in the alkyl portion, a cycloalkyl group, an aryl group, a hexose group linked as an ester, or a chain of 2–6 hexose groups, provided firstly that in those compounds of the formula I or II where R is a hydrogen atom, a methyl group, or an ethyl group, and R¹ is hydrogen or a methyl group, and Z is hydrogen, then the groups X and Y are not collectively two hydrogen atoms, two chlorine atoms, two bromine atoms, two methoxy groups, or a group of the formula —O—CH₂—O—, and where X is hydrogen then Y is not an iodine atom, a hydroxy group, a methoxy group, or a methyl group, provided secondly that in those compounds of the formula I or II, where Z, X and Y are hydrogen atoms and R is hydrogen, a methyl group, an ethyl group, or a butyl group, then R¹ is not a methyl group, a butyl group, a benzyl group, an acetyl group or a 4-chlorobenzoyl group, and provided thirdly that in those 2-oxo-1,2,3,4-tetrahydroquinoline-4-carboxylic acids of formula II where Z is an ethyl group, then at least one of R, R¹, X and Y is not a hydrogen atom.

13. A pharmaceutical composition as in claim 12, comprising esters of formula I or II, wherein R is an alkyl group with 3–6 carbon atoms, an aralkyl group with 1–6 carbon atoms in the alkyl portion and a phenyl group in the aryl portion, a cycloalkyl group with 3–7 carbon atoms, a phenyl group, a hexose group linked as an ester, or a group of 2–6 hexose groups, provided that where R¹ is a butyl group and Z, X and Y are hydrogen, then R is not a butyl group.

14. A pharmaceutical composition as in claim 12, wherein

R is hydrogen, and

Z is an alkyl group with 1–6 carbon atoms, an aralkyl group with 1–6 carbon atoms in the alkyl portion, a cycloalkyl group with 3–7 carbon atoms, or an aryl group, provided that where Z is an ethyl group, then at least one of $R^1$, X and Y is not a hydrogen atom.

15. A pharmaceutical composition as in claim 12, wherein at least one of X and Y comprise an alkyl group with at least two carbon atoms, a cycloalkyl group, a phenyl group, a nitro group, an alkoxy group with at least two carbon atoms, or an ester group of the formula

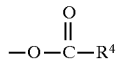

wherein $R^4$ is an alkyl group with 1–6 carbon atoms, an aryl group, or a cycloalkyl group with 3–7 carbon atoms, provided that where one of R, Z, and $R^1$ is not a hydrogen atom, then X and/or Y comprise methyl groups and/or methoxy groups, and provided that where in formula I, Z and $R^1$ are hydrogen, and R is methyl and both X and Y are methoxy groups, then X and Y are not situated in positions 5 and 6.

16. A pharmaceutical composition including as the pharmaceutically active agent 2-oxindole-3-acetic acid of formula I

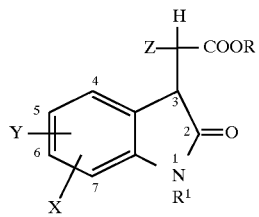

wherein $R^1$ is a hydrogen atom, an alkyl group with 1–6 carbon atoms, an aralkyl group with 1–6 carbon atoms in the alkyl portion, a cycloalkyl group, or an acyl group of the formula

wherein $R^4$ is a hydrogen atom, an alkyl group with 1–6 carbon atoms, an aralkyl group with 1–6 carbon atoms in the alkyl portion, an aryl group, or a cycloalkyl group, Z is a hydrogen atom, an alkyl group with 1–6 carbon atoms, an aralkyl group with 1–6 carbon atoms in the alkyl portion, a cycloalkyl group, or an aryl group, and X and Y represent independently of one other hydrogen atoms, alkyl groups, cycloalkyl groups, aryl groups, hydroxy groups, halogen atoms, nitro groups, ether groups of the formula

ester groups of the formula

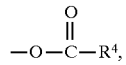

or ester groups of the formula

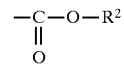

wherein $R^4$ is a hydrogen atom, an alkyl group with 1–6 carbon atoms, an aralkyl group with 1–6 carbon atoms in the alkyl portion, an aryl group, or a cycloalkyl group; $R^2$ is an alkyl group with 1–6 carbon atoms, an aralkyl group with 1–6 carbon atoms in the alkyl portion, a cycloalkyl group, or an aryl group or groups, or X and Y together represent a group of the formula

in which n is an integer in the range of 1–4, and

R is a hydrogen atom, an alkyl group with 1–6 carbon atoms, an aralkyl group with 1–6 carbon atoms in the alkyl portion, a cycloalkyl group, an aryl group, a hexose group linked as an ester, or a chain of 2–6 hexose groups.

17. A pharmaceutical composition as in claim 16, including as the pharmaceutically active agent a compound of formula I wherein Z and $R^1$ are hydrogen atoms, R is a hydrogen atom, an alkyl group with 1–6 carbon atoms, a cycloalkyl group with 3–8 carbon atoms, or a phenyl group, and X and Y represent independently of one another hydrogen atoms, hydroxy groups, halogen atoms, nitro groups, ether groups of the formula

or ester groups of the formula

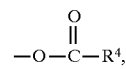

wherein $R^2$ is an alkyl group with 1–6 carbon atoms or a phenyl group; $R^4$ is an alkyl group with 1–6 carbon atoms, a phenyl group, or a cycloalkyl group with 3–7 carbon atoms.

18. A pharmaceutical composition as in claim 16 including as the pharmaceutically active agent a racemate of the compound of formula I, such racemate enriched with an enantiomer of formula I, or an enantiomer of formula I.

19. A pharmaceutical composition as in claim 12 wherein R, Z, X, Y and $R^1$ are all hydrogen atoms.

20. A pharmaceutical composition as in claim 17, including as the pharmaceutically active agent a racemate of the compound of formula I, such racemate enriched with an enantiomer of formula I, or an enantiomer of formula I.

21. A pharmaceutical composition as in claim 18 wherein R, Z, X, Y and $R^1$ are all hydrogen atoms.

22. A method of modulating the immune reaction of a warm-blooded animal including the step of administering to the animal a daily dosage of between 0.02 and 0.06 milligram per kilogram of body weight of a pharmaceutical composition comprising as the pharmaceutically active agent 2-oxindole-3-acetic acid of formula I or 2-oxo-1,2,3,4-tetrahydroquinoline-4-carboxylic acid of formula II

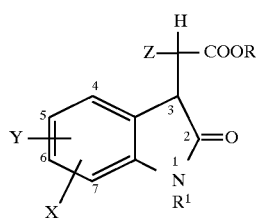

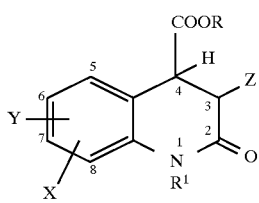

wherein

R[1] is a hydrogen atom, an alkyl group with 1–6 carbon atoms, an aralkyl group with 1–6 carbon atoms in the alkyl portion, a cycloalkyl group, or an acyl group of the formula

wherein R[4] is a hydrogen atom, an alkyl group with 1–6 carbon atoms, an aralkyl group with 1–6 carbon atoms in the alkyl portion, an aryl group or a cycloalkyl group;

Z is a hydrogen atom, an alkyl group with 1–6 carbon atoms, an aralkyl group with 1–6 carbon atoms in the alkyl portion, a cycloalkyl group, or an aryl group, and X and Y represent independently from each other hydrogen atoms, alkyl groups, cycloalkyl groups, aryl groups, hydroxy groups, halogen groups, nitro groups, ether groups of the formula

ester groups of the formula

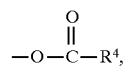

or ester groups of the formula

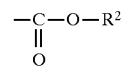

wherein R[4] is a hydrogen atom, an alkyl group with 1–6 carbon atoms, an aralkyl group with 1–6 carbon atoms in the alkyl portion, an aryl group or a cycloalkyl group; R[2] is an alkyl group with 1–6 carbon atoms, an aralkyl group with 1–6 carbon atoms in the alkyl portion, a cycloalkyl group, or an aryl group or groups, or X and Y together represent a group of the formula

in which n is an integer between 1–4, and

R is a hydrogen atom, an alkyl group with 1–6 carbon atoms, an aralkyl group with 1–6 carbon atoms in the alkyl portion, a cycloalkyl group, an aryl group, a hexose group linked by an ester, or a chain of 2–6 hexose groups.

* * * * *

UNITED STATES PATENT AND TRADEMARK OFFICE
CERTIFICATE OF CORRECTION

PATENT NO. : 5,849,756
DATED : December 15, 1998
INVENTOR(S) : Ulrich Burger et al It is certified that error appears in the above-indentified patent and that said Letters Patent is hereby corrected as shown below:

In Claim 16, col. 19, line 55,
  delete "other" and substitute therefor --another--.

In Claim 16, col. 20, line 15, please correct the third parenthesis, delete the formula:

$$-O-(CH_2)_n-)-$$

and substitute therefor the formula:

$$-O-(CH_2)_n-O-$$

In Claim 19, col. 20, line 52,
  delete "12" and substitute therefor --17--.

Signed and Sealed this

Eleventh Day of May, 1999

Attest:

Q. TODD DICKINSON

*Attesting Officer*      *Acting Commissioner of Patents and Trademarks*